United States Patent [19]

Ribi

[11] Patent Number: 5,156,810
[45] Date of Patent: Oct. 20, 1992

[54] BIOSENSORS EMPLOYING ELECTRICAL, OPTICAL AND MECHANICAL SIGNALS

[75] Inventor: Hans O. Ribi, Mateo, Calif.

[73] Assignee: BioCircuits Corporation, Burlingame, Calif.

[21] Appl. No.: 366,651

[22] Filed: Jun. 15, 1989

[51] Int. Cl.$^5$ .............. G01N 33/53; G01N 27/00; G01N 21/01
[52] U.S. Cl. .............. 422/82.01; 422/82.02; 422/82.06; 435/291; 436/501; 436/527; 436/531; 436/806; 204/403
[58] Field of Search .............. 422/82.01, 82.02, 82.03, 422/82.06; 436/806, 527, 501, 531; 435/291, 817; 204/403

[56] References Cited

U.S. PATENT DOCUMENTS

| | | | |
|---|---|---|---|
| 4,444,878 | 4/1984 | Paulus | 204/403 |
| 4,444,892 | 4/1984 | Malmros | 436/806 |
| 4,489,133 | 12/1984 | Kornberg . | |
| 4,490,216 | 12/1984 | McConnell | 435/817 |
| 4,560,534 | 12/1985 | Kung et al. | 422/82.02 |
| 4,632,800 | 12/1986 | Barraud et al. . | |
| 4,661,235 | 4/1987 | Krull et al. | 435/291 |
| 4,824,529 | 4/1989 | Thompson et al. | 435/291 |
| 4,857,273 | 8/1989 | Stewart | 435/291 |
| 4,960,722 | 10/1990 | Ogawa | 435/291 |

OTHER PUBLICATIONS

Yager, U.S. Statutory Invention Registration H201, Jan. 1987.
Haddon and Lamola in *Proc. Natl. Acad. Sci. USA* (1985) 82:1874–1878.
Arrhenius, et al., *Proc. Natl. Acad. Sci. USA* (1986) 83:5355–5359.
E. G. Wilson in *Electronics Letters* (1983) 19:237.
J. R. Reynolds in *Journal of Molecular Electronics* (1986) 2:1–21.
V. M. Owen in *Ann. Clin. Biochem.* (1985) 22:559–564.
Bader et al., *Advances in Polymer Science* (1985) 64:1–62.
Marti et al., *Science* (1988) 239:50–52.
Michio Sugi in *Journal of Molecular Electronics* (1985) 1:3–17.
Lochner, et al. in *Phys. Stat. Sol.(b)* (1978) 88:653–661.
Thompson and Krull in *Trends in Analytical Chemistry* (1984) 3(7):173–178.

Primary Examiner—James C. Housel
Assistant Examiner—Jan M. Ludlow
Attorney, Agent, or Firm—Bertram I. Rowland

[57] ABSTRACT

Biosensors are provided employing a thin crystalline diyne surfactant polymeric electrically conducting layer to which may be bound members of specific binding pairs. Binding of an analyte or a reagent to the specific binding pair member layer may change the electrical, optical or structural properties of the layer for measurement of analyte. The change in the polymeric layer provides for a sensitive measurement.

8 Claims, 2 Drawing Sheets

VAPOR DEPOSITION
OF METAL ELECTRODES
ON INSULATING SURFACE
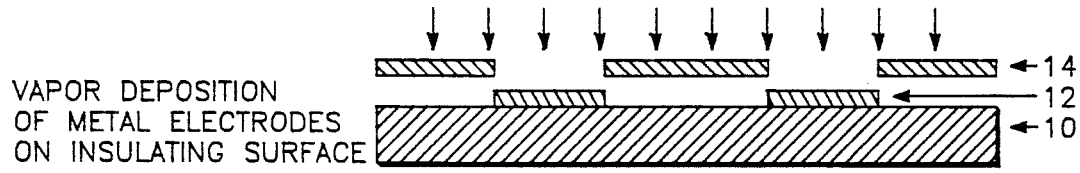
FIG.−1A
TRANSFER OF ULTRA−
THIN CONDUCTING
POLYMER FILM
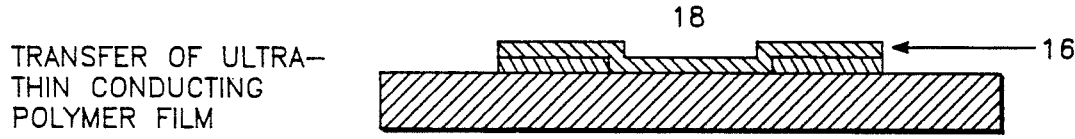
FIG.−1B
INSULATION OF METAL
ELECTRODES WITH
RESISTIVE MATERIAL
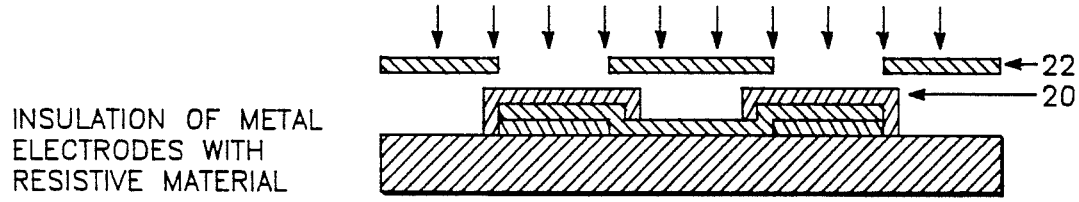
FIG.−1C
IOLOGICAL ACTIVATION
OF POLYMER FILM WITH
SPECIFIC RECEPTORS
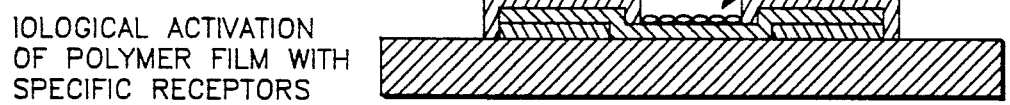
FIG.−1D
SEALING OF
ADDRESSABLE SENSOR
REGIONS
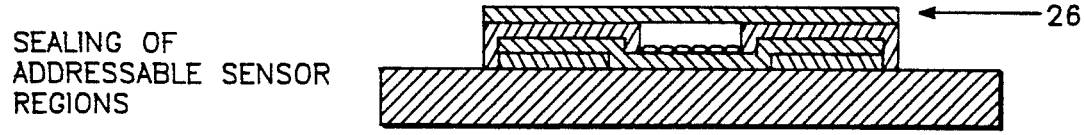
FIG.−1E

BIOSENSORS EMPLOYING ELECTRICAL, OPTICAL AND MECHANICAL SIGNALS

TECHNICAL FIELD

The field of the subject invention is biosensors employing electrically conducting polymer surfactant layers for detection of analytes.

BACKGROUND

In the last two decades there has been an increasing awareness of the need to assay for the presence of a large number of different types of analytes, as well as in many cases to be able to quantitate a particular analyte. During the 70's, a number of different chemistries were developed to avoid the need to use radioisotopes, where RIA was the primary technique for detecting a specific ligand or receptor. A wide variety of labels have been developed which would appear to have reached their ultimate degree of sensitivity in conjunction with the protocols and intrumentation that has been available. While much of the effort has been directed to developing intrumentation which can handle a large number of assays in a substantially automated manner, the market for low volume assays for a variety of different ligands has been increasingly expanding. The need for this market is to be able to perform an extended number of assays for different ligands in relatively low numbers for each ligand and with a minimum of technical competence. Therefore, in many cases, the protocol for the preparation of the sample should be simple and pretreating of the sample should be relatively routine.

To answer the increasing need for detection of ligands, there have been numerous developments to improve instrumentation in combination with particular chemistries. Thus, there are a number of available instruments which are reasonably sensitive, have a relatively low requirement of technical competence, and the newer instrumentation is less expensive than prior instrumentation. Nevertheless, for many aspects of the market, there still remains an important need for a simple, efficient and inexpensive device, which allows for the sensitive detection of low levels of ligands in a variety of media.

RELEVANT LITERATURE

U.S. Pat. No. 4,489,133 describes procedures and compositions involving orderly arrays of protein molecules bound to surfactants. Thomas, et al., *Electron. Letters* (1984) 20:83-84 describe a GaAs/LB film MISS switching device employing ω-tricosenoic acid as the surfactant bilayer for producing a thin insulator Lochner, et al., *Phys. Status Solidi* (1978) 88:653-661 describe photoconduction in polydiacetylene multilayer structures and single crystals. Sugi, *J. Molecular Electronics* (1985) 1:3-17 provides a review of Langmuir-Blodgett film use in electronics. Reynolds, ibid (1986) 2:1-21 describes conducting organic polymers. Wilson, *Electron. Letters* (1983) 19:237 describes the principles of a three dimensional molecular electronic memory employing polydiacetylene crystals or Langmuir-Blodgett multilayer films. Descriptions of electronic devices employing organized macromolecular ensembles formed with surfactant layer crystallization include Arrhenius, et al., *Proc. Natl. Acad. Sci. USA* (1986) 83:5355-5359; Haddon and Lamola, ibid (1985) 82:1874-1878; and Paleos, *Chem. Soc. Rev.* (1985) 14:45-67. Vandevyer, et al., *J. Chem. Phys.* (1987) 87:6754-6763. U.S. Pat. No. 4,624,761. Fujiki, et al., *Amer. Chem Society* (1988) 4:320-326. Biegajski, et al., *Amer. Chem Society* (1988) 4:689-693. Pecherz, et al., *Journal of Molecular Electronics* (1987) 3:129-133. Lando, et al., *Synthetic Metals* (1984) 9:317-327. Day, et al., *Journal of Applied Polymer Science* (1981) 26:1605-1612. Shutt, et al., *Amer. Chem. Society* (1987) 3:460-467. Dhindsa, et al., *Thin Solid Films* (1988) 165:L97-L100. Metzger, et al., *Amer. Chem. Society* (1988) 4:298-304. Fujiki, et al., *Amer. Chem. Society* (1988) 4:320-326. Wohltjen, et al., *IEEE Transactions on Electron Devices* (1985) 32:1170-1174. Wernet, et al., *Semiconducting L-B Films* (1984) 5:157-164. Sugi, et al., *Thin Solid Films* (1987) 152:305:326. Peterson, *Journal of Molecular Electronics* (1986) 2:95-99. Descriptions of methods for immobilizing biological macromolecules on polymerized surfactant films include: O'Shannessey, et al., *J. Appl. Bioch.* (1985) 7:347-355. Hashida, et al., *J. Appl. Biochem.* (1984) 6:56-63. Packard, et al., *Biochem.* (1986) 25:3548-3552. Laguzza, et al., *J. Med. Chem.* (1989) 32:548-555. Jimbo, et al., *Journal of Molecular Electronics* (1988) 4:111-118. Hanifeld, *Science* (1987) 236:450-453. Goundalkar, *Communications* (1984) 36:465-466. Cress, et al., *Amer. Biotec. Lab.* (February 1989) 16-20. Biosensors employing surfactant layer crystallization are described by Owen, *Ann. Clin. Biochem.* (1985) 22:555-564 and Thompson and Krull, *Trends in Anal. Chem.* (1984) 3(7):173-178. Bader, et al., *Advances in Polymer Sci.* (1985) 64:1-62 describe polymeric monolayers in liposomes as models for biomembranes.

SUMMARY OF THE INVENTION

Biosensors are provided comprising an electrically inert substrate, an electrically conductive surfactant layer, and bound to the surfactant layer, members of a specific binding pair. The specific binding pair members may be present as a uniformly oriented layer. Analytes are detected by binding to the bound specific binding pair member, resulting in a change in electrical signal, light modulation or structural modulation resulting from a change in the surfactant layer. Specific methods of fabrication and application are described for the biosensor.

BRIEF DESCRIPTION OF THE DRAWINGS

FIGS. 1A-1E are schematic views of a process for preparation of a biosensor.

DESCRIPTION OF THE SPECIFIC EMBODIMENTS

Figure 2:
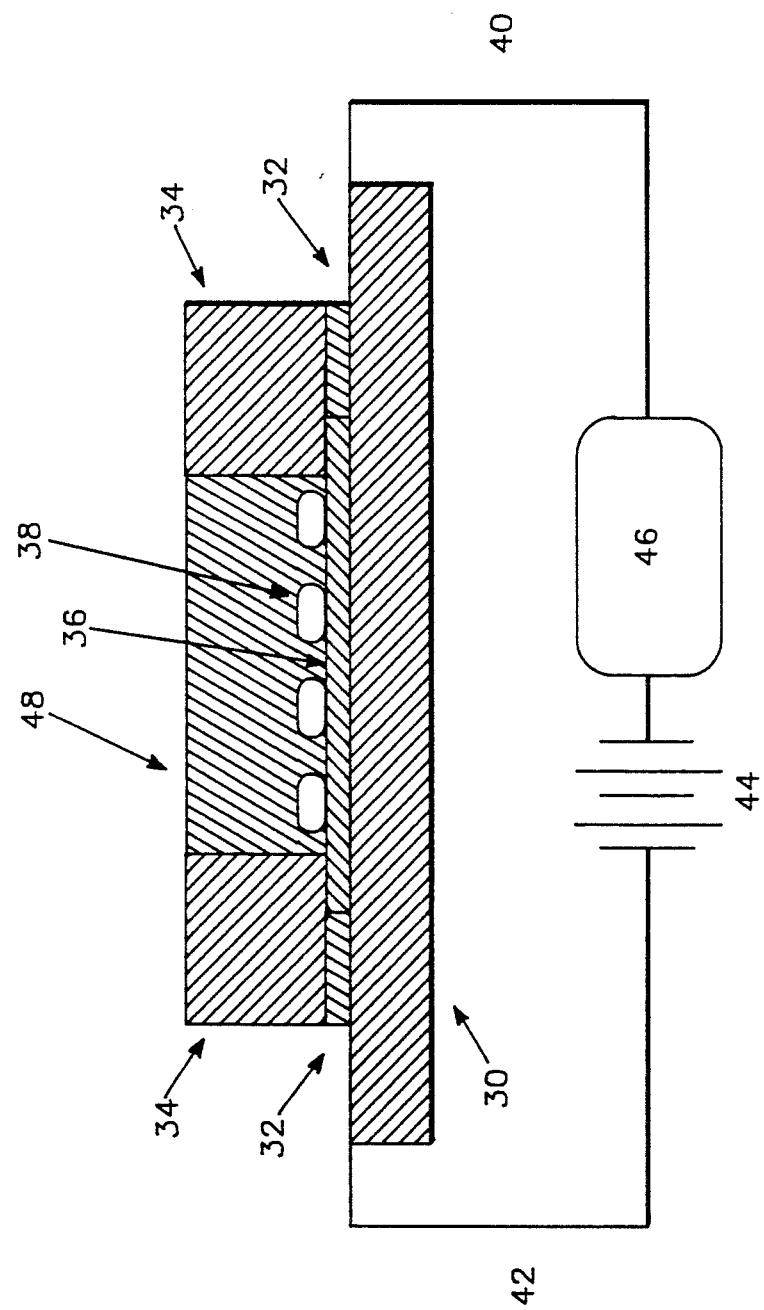
FIG. 2 is a diagrammatic design of a circuit and biosensor.

Biosensor devices and compositions associated with such devices are provided for the detection of analytes. The biosensors comprise a solid substrate upon which is formed a highly oriented surfactant film, which is electrically conducting as a result of polymerization of polyunsaturated groups in the surfactant. Joined to the surfactant molecules distal from the substrate are members of a specific binding pair, which directly or indirectly may interact with the analyte of interest. Binding of the analyte of interest perturbs the surfactant layer, so as to allow for detection of the presence of the analyte by a change in an electrical, structural, or light signal. While not wishing to be bound to any theory, it appears that there is a change in conformation of the surfactant layer.

The members bound to the surfactant layer may be a uniformly oriented layer, where the molecules are substantially contiguous, even crystalline, or may be separated to form a non-contiguous layer, so long as binding of the analyte to the specific binding member provides for a change in the surfactant layer which allows for detection of the presence of the analyte.

Depending upon the particular protocol, the substrate may take many different forms. The substrate may comprise a semiconductive layer, which allows for detection of photons. The semiconductive layer will usually be separated from the surfactant layer by a transparent layer. This transparent layer may serve solely as a support for the surfactant layer and a separator between the surfactant layer and semiconductive layer, as a filter to limit the wave length range of light which passes through the substrate, or the like. The substrate may be a reflective substrate which allows for reflection of light through the surfactant layer to the substrate surface and then back through the surfactant layer. Alternatively, the substrate may serve solely as an electrical insulating support for the surfactant layer providing for protection and mechanical rigidity to the surfactant layer.

Various substrates may be employed, particularly insulating materials. The substrate needs to be inert and have good electrical insulating properties. It should be smooth at the molecular level, and have good adhering properties. The substrate has to be readily available and inexpensive. Prescoring and dicing might be necessary in order to manufacture the device. The substrate can be made out of different materials e.g., glass, plastics, silicon, hydrocarbons, wax, alkylated surfaces, or the like. The materials of choice are highly electrically resistive glasses or polymers. Glasses include borosilicate, low expansion glasses such as Corning number 7095, Tempax, and other highly resistive glasses. A wide variety of organic polymers may be employed, particular hydrocarbon polymers, such as polyethylene, polypropylene, polystyrene, etc. or condensation polymers, such as polyterephthalate, polyacrylate, polyformaldehyde, or the like.

The thickness of the substrate may vary widely, depending upon the total number of layers and their thickness and nature, the structure of the biosensor chip element, the architecture, and the like. Usually, the thickness will be at least about 5 mil and not more than about 500 mil, usually not more than about 100 mil. However, the particular thickness will usually not be critical, so long as it does not interfere with the operation of the chip and provides the desired structural support. The surface of the substrate which serves to receive the surfactant layer and will be in contact with the surfactant layer should be clean and free of dirt and dust to minimize imperfections in the formation of the layer. For transferring polymerized surfactant films to the substrate by abutting the hydrophobic surface of the film to the substrate requires that the substrate be made hydrophobic. One process for making glass hydrophobic involves alkylation. An example of alkylation involves the use of a 5% solution of an alkylating agent in hexane. The agent can be a carbon chain with 1–50 carbons, usually 1–18, containing a methylalkylhalide silane group. For example, dimethyloctadecylchlorosilane may be used. After dipping and air drying, the glass is washed several times in chloroform, air dried, rinsed in high purity water for several minutes, and then air-dried again. The washing steps may be repeated several times.

Surfactant films are formed on the surface of an aqueous subphase by standard lipid monolayer technologies. A solution containing a monomeric surfactant composition, dissolved in an organic solvent, is applied to the subphase surface by a micropipet. Solvents may include hydrocarbons such as pentane, hexane, heptane, and decane. The hydrocarbons may be straight chain, branched or unsaturated. Solvents may include chlorocarbons such as mono-, di-, tri- or tetrachloromethane. The addition of more polar solvents such as alcohols, furans, ethers, esters, or the like may be added to enhance the solubility of the surfactant composition.

The subphase composition dictates the physical characteristics of the surfactant layer which is formed. The subphase can be composed of pure water, glycerol, polyethylene glycol, or other polar organic solvents miscible with water including DMF, DMSO, acetone, alcohols, ketones, furans, dioxane, ethanolamine, phenols, alone or in combination or the like. High boiling point solvents such as glycerol will prevent evaporation during heating, while low boiling point solvents will enhance the evaporation. Other organic solvents can be used to stabilize the surfactant film, particularly to favorably interact with the polar headgroups, linkers and ligands of the surfactant. The subphase can also contain organic or inorganic acids or bases which affect the surfactant film through ionic interactions, i.e., charge stabilization. The ionic components can include mono- and polyvalent ions and cations, and mono- and oligosaccharides.

Monomeric polymerizable surfactants are spread on the subphase at a concentration ranging from 0.01 to 50 milligrams/milliliter of spreading solvent. Typically 0.1 to 1.0 milligram/milliliter is most useful. Films are usually formed with a mixture of polymerizable surfactants including surfactant-linked-ligands and filler surfactants which have no ligand attached. The polymerizable moiety of the filler surfactant is typically similar or identical to that of the ligand containing surfactant. The filler surfactant may have all the chemical characteristics of the ligand surfactant. It should have polar headgroups which are biologically inert and resilient to non-specific binding. As an example, the filler surfactant may have a hydroxyl, polyhydroxyl or polyethylene oxide headgroup which acts to prevent non-specific adherence of biological matter. The filler lipid could also contain a chromophore for enhancing the optical visualization of the film, and to enhance the photoelectrical injection of light. The mole percentage incorporation of the ligand-surfactant to the filler-surfactant plays a role in the support matrix. It is generally from 0.01 to 90%, more usually from 0.1–10% and usually in the range of 1.0 to 5%. The composition of the polar headgroup of the filler-lipid can modulate the specific binding of biological material. Steric displacement can enhance protein binding, and steric hindrance could inhibit protein binding. The composition of the polar headgroup of the filler-lipid can thus provide a control mechanism for adjusting binding affinities and interactions.

Film formation involves applying a subphase to a surface or well. A solution containing the monomeric surfactant is applied to the subphase surface until the surface is substantially saturated. Dried islands of surfactants will normally become apparent. The aqueous medium is then heated to melt the surfactant, usually to a temperature of not more than about 100° C., which results in disappearance of the islands. Once the islands have dissolved, the medium is allowed to cool to room temperature, followed by further cooling to below room temperature, usually to about 2° C. The formation of high quality films requires that the monomeric surfactant is highly crystalline at the gas/subphase interface. Crystalline films are often comprised of tightly packed single crystal domains. Large domains are desirable for manufacturing processes. Factors found to affect the domain size are crystallization temperature spreading solvent composition, and spreading solvent amount. The crystal growth can be initiated and controlled using a number of methods such as zone refinement, later film pressure, crystal reannealing processes, site specific nucleation, the use of seed crystals, controlled atmospheric conditions, epitaxial crystallization, varying subphase composition, or the like. Large single crystals may be nucleated by initially crystallizing a surfactant film and then irradiating a narrow width of film using an intense UV laser source. When the subphase temperature is raised above the surfactant melting temperature, the non-polymerized regions of film will become fluid. When the subphase is cooled back below the surfactant melting transition, crystals of monomers nucleate from the crystalline polymer region.

The surfactant is then polymerized employing any convenient initiation system, e.g., ultra-violet light. Other initiation systems include combinations of light and light sensitive initiators, heat labile chemical initiators or the like. Such initiators are conventional and need not be described here. The activation is maintained until at least substantially complete polymerization is achieved. Polymerization may also be carried out by using high energy light including electron beams, X-ray sources and other synchotron radiation. One method of polymerization involves site localized polymerization using focused laser light and an XY-controlled positioner, for the purpose of patterning circuits into the film [Ogawa, et al., *Langmuir* (1988) 4:195].

The film quality can be inspected optically using methods such as polarization birefringence, lateral diffusion techniques including lateral film pressure, or fluorescent measurements such as fluorescent recovery after photo bleaching. Films are inspected for defects, crystal domain size and shape, and integrity. Defects may include point defects, edge defects, breakage, fractures. Crystal domain size and shape is characterized by various crystalline features such as dendritic patterns, large intact defect free domains, crystalline compactness and crystalline orientation. The film may be transferred to different substrates for production of the biosensor. Transfer is achieved by applying standard Langmuir-Blodgett methods [George L. Gaines Jr.: Insoluble Monolayers at Liquid Gas Interfaces, Interscience Publishers, I. Prigogine Editor, John Wiley and Sones (1964)].

The substrate with the electrodes on the surface is placed in contact with the polymer film such that the hydrophobic surface of the substrate interacts with the hydrophobic surface of the polymerized surfactant film. Good contact between the substrate and the surfactant film results in a stable complex. The transfer can occur by vertically dipping the substrate through the subphase surface, or by placing the substrate horizontally on top of the subphase surface. Alternatively, the surfactant film can be transferred so that its hydrophilic surface is placed in intimate contact to a hydrophilic substrate. This approach requires that the substrate be lifted from beneath the subphase surface and be pulled out so that the film coats the substrate. Multilayers of polymer film can be deposited onto the substrate for various purposes, including films for non-linear optical devices, increased electrical conductivity through multiple films, and the building of complex layers of protein films and surfactant films for molecular electronic devices.

The polymerizable surfactants have been extensively described in the literature as evidenced by the prior art described previously. The composition of the surfactant layer may be homogenous, where the surfactant is polymerizable and has a polar terminus, which may serve as a ligand for a complementary binding protein, or heterogenous, where a mixture of surfactants are employed, some of which are polymerizable and others are not polymerizable. The polymerizable and/or non-polymerizable surfactants may be the site for binding to a ligand.

The surfactant molecule may have a single lipid chain, e.g., a diynoic acid or a plurality of lipid chains, e.g., diester glycerides, preferably a single chain, and generally not more than two lipid chains.

Illustrative surfactants include 6, 8-hexadecadiynoic acid, 2-hydroxyethyl octadeca-8-10-diynoate, eicosa-12,14-diynyl-10,12-phosphatidyl serine, pentaeicosa-10,12-diynoic acid, tricosa-10,12-diynoic acid, acetylene compounds with multiple diyne groups and other polymer surfactants including single acyl chain polyerizable surfactants.

Various other surfactants may be present as diluents for the polymerizable surfactant. These surfactants may be naturally occurring, synthetic, or combinations thereof, and may be illustrated by laurate, stearate, arachidonate, cholesterol, bile acids, gangliosides, sphingomyelins, cerebrosides, or the like.

Various functional groups may be present in the film to provide for polymerization, which allow for electron transfer. For the most part, the functional groups will comprise monoynes and diynes, although other polyunsaturated molecules may find use, such as activated monoynes, e.g., $\alpha$-ketomonoynes.

For the most part, the hydrophobic portion of the surfactant will have a chain of at least 6 aliphatic carbon atoms, usually a straight chain of at least 6 aliphatic carbon atoms, and generally not more than a total of about 100 carbon atoms, usually not more than about 30 carbon atoms. Preferably, the number of carbon atoms will vary from about 12 to 26, more usually 14 to 26, and more preferably 16 to 24 carbon atoms.

The hydrocarbon can have attached florescent dyes, electron donor or acceptor groups, and groups which dope the polymer chain for increased electric conductivity. For the purpose of enhancing film stability, the hydrocarbon chain can be fluorinated, or mono- or polyhalogenated. Halogenation is known to affect hydrocarbon chain packing and increase film melting transitions.

The lipid molecules will terminate in a hydrophilic moiety, cationic, anionic or neutral (nonionic) where the functionalities may include non-oxo carbonyl, e.g., carboxylic acids, esters and amides, oxo-carbonyl, such as aldehydes or ketones, oxy, such as ethers, polyethers, and hydroxyl, amino, such as primary, secondary, and tertiary amines and ammonium, phosphorus acids esters and amide, such as phosphate, phosphonate, and phosphonamide, sulfur functionalities, such as thiol, sulfonates, sulfate, and sulfonamides, and the like. Hydrophilic groups may include drugs or chromophores. Usually, the polymerizable functionality will be separated from the polar and non-polar termini by at least one carbon atom, generally from about 1 to 50 carbon atoms, more usually from about 1 to 8 carbon atoms. The polymerizable group is typically incorporated into the hydrophobic interior of the surfactant film. Examples of polymerized groups include polypyrrole, polyamlines, polythiophene, poly(isothianaphthene) poly(alkylthiophene), polydiacetylene, polyacetylene, or the like. Diacetylenic groups may also be incorporated in the hydrocarbon chain of the surfactant so that more than one group is present for polymerization. By having two or more polymerizable groups in the surfactant chain, a multiplicity of electrically conducting polymers may be obtained. This configuration leads to films of higher conductivity and mechanical strength. The individual polymerizable groups can be spaced at regular intervals from 1-50 carbons apart, typically 2-10 carbon atoms apart. There can be as many of these groups in the chain as its length allows. Variations of the headgroup provides for improved film quality, such as stability of the film, surface charge, reduction of non-specific binding or fluid matrix effects, and ease of chemical modifications. The hydrocarbon tail of the surfactant may also terminate in a hydrophilic group so that the surfactant is bipolar. [Sher, *Justus Liebigs Ann. Chem.* (1954) 589:234; and Akimoto, et al. *Angew. Chem.* (1981) 20(1):91].

Depending upon the desired density of the ligand bound to the surfactant, the ligand may be present in from about 1 to 100 mol % of surfactant, more usually at least about 5 mol %, and preferably at least about 20 mol %, generally not more than about 80 mol %. The mol ratio will depend on the size and nature of the ligand, whether contiguous ligands are desired in the layer, and the like. The ligands may be joined by any convenient functionality, including esters, e.g., carboxylate and phosphate, ethers, either oxy or thio, amino, including ammonium, hydrazines, amides, such as carboxamide, sulfonamide or phosphoramide, combinations thereof, or the like. Specific groups may involve saccharides, both mono- and polysaccharide, including aminosaccharides, carboxysaccharides, reduced saccharides, or the like. Specific groups include zwitterions, e.g., betaine, sugars, such as glucose, glucuronic acid, $\beta$-galactosamine, sialic acid, etc, phosphatidyl esters, such as phosphatidyl glycerol serine, inositol, etc.

The ligand can be any small molecule containing a reactive group. Typical ligands could be biotin, drugs such as alkaloids, antigens, polysaccharides, polypeptides, polynucleotides, ionic groups, polymerizable groups, linker groups, electron donor or acceptor groups, hydrophobic groups, or hydrophilic groups. The ligand may also serve as a site which can be further chemically modified to bring about new physical features or film characteristics.

The ligand can also be a photoactivateable or photocleavable group, in which case the possibility of biosensors for panel testing becomes very attractive. Using photoactivation or photocleavage and masking, one can selectively bind different receptors, antibodies, drugs or the like to the same biosensor, presenting tremendous advantages for panel testing or screening. Some of the advantages would be ease of screening, by simultaneously testing without extra steps, and cost. These panels could be used in research or in industry, for receptor testing, monoclonal antibody screening, therapeutic drug discovery, in diagnostics for cancer screening, testing of drugs of abuse or therapeutic drugs, urinary tract infections, and sexually transmitted disease testing. The biosensor can also be used for environmental testing, in the food industry, and the like. A reusable biosensor panel could be incorporated into a flow cytometry instrument or other such instruments.

The articles of this invention can be prepared, for the most part, using conventional techniques employing particular conditions to achieve the desired layers. For the most part, Langmuir-Blodgett techniques will be employed as described in the references cited previously. In employing the subject methods, attention should be given to the experimental section for guidance as to the particular range that should be used with any particular parameter for the desired result.

A large number of parameters are available which can be used to influence the nature of the product. These parameters include the buffer, including pH, ionic strength, cations employed, e.g., mono- or polyvalent, composition of the surfactant, both as to the polymerizable surfactant and the nonpolymerizable surfactant, including such considerations as chain length, the status of the polymerizable functionality, the nature of the polymerizable functionality, and the nature of the polar head group; the manner in which the surfactant layer is formed, including concentration of surfactant and solvent, the nature of the solvent, the spreading method, and the amount of surfactant employed, which will affect the formation of multilamellar layers; and physical parameters, such as film tension, crystallization time, temperature, humidity, E (electric) field, and M (magnetic) field (protein dipole moment).

The ligands which are covalently bonded to the surfactant will normally be a member of a specific binding pair. Thus, the ligands may be varied widely, usually being molecules of less than about 2 kDal, more usually less than about 1 kDal. For the most part, the ligands will be considered to be haptenic, which may include small organic molecules, including oligopeptides, oligonucleotides, saccharides or oligosaccharides, or the like. However, in some situations, the ligand bound to the surfactant may be a macromolecule, usually not exceeding about 500 kDal, more usually not exceeding about 200 kDal. Thus, proteins, nucleic acids, or other polymeric or nonpolymeric compounds of high molecular weight may also be employed. There is also the possibility to use crown ethers which will bind to particular ions. The particular manner in which one or more surfactants may be bound to the ligand is not critical to this invention and will depend, for the most part, on convenience, ease of synthesis, stability, available functional groups, and the like. Synthetic macrocyclic complexes may be incorporated into the surfactant layer for the purpose of molecular recognition of various natural and non-natural compounds.

The ligand may be a molecule which can provide for covalent binding to another molecule. Carboxy groups may be activated with carbodiimide to react with alcohols, phenols and amines. Hydrazines may react with carboxylic acids, ketones and aldehydes, particularly under reducing conditions. Thiols can react with activated olefins, such as maleimide, acrylates, etc. or activated halides, e.g., $\alpha$-chloroacetyl, and the like. For non-covalent or covalent binding, some enzyme substrates, inhibitors or suicide inhibitors may be employed with the complementary enzyme.

In many cases, particular ligands will be used for a variety of purposes. For example, biotin may be used to bind to avidin or strepavidin, where the complementary member may then be used to link a wide variety of other molecules. Various lectins may be employed to bind a variety of sugars which may be attached to molecules of interest. Specific ligands may be employed which bind to complementary receptors, such as surface membrane receptors, soluble receptors, or the like.

Of particular interest is the binding of receptor, either directly or indirectly, to the surfactant. Direct binding will usually be covalent, while indirect binding will usually be non-covalent. Receptors of particular interest will be antibodies, which include IgA, IgD, IgE, IgG and IgM, which may be monoclonal or polyclonal. The antibodies could be intact, their sulfhydryl bridges totally or partially cleaved, fragmented to $Fab_2$ or Fab, or the like. The intact and totally cleaved antibodies could be used to make a recombinant protein A-antibody hybrid, to be incorporated into the assay. Coupling through the antibody's oligosaccharide moiety to hydrazines can be achieved with the intact, partially and totally cleaved antibody. Maleimide linkages could be used for the intact, partially and totally cleaved antibodies, and the $Fab_2$ fragment, while the Fab fragment could be incorporated in an antibody hybrid. Other examples for antibody coupling to polymer films will include the use of recombinant hybrid linker proteins and recombinant antibody molecules. The antibodies may be functionalized at the Fc portion to ensure the availability of the binding sites for further binding.

The electrode substrate may be smaller than 1 $\mu m^2$, and as large as 10 $cm^2$, the size not being critical. A large sheet having scored regions may be employed, where the individual wafers may be separated after processing. The electrode substrate which receives the surfactant layer may be prepared in a variety of ways. Conveniently, vapor deposition or sputtering of metal electrodes may be employed by placing a prescribed metal stencil with the desired electrode configuration over an insulating substrate. The stencil covered substrate is placed in a vacuum sputtering apparatus, where gold, silver, platinum, aluminum, or a combination of metals is placed in the evaporation boat and the apparatus evacuated to a low pressure, generally equal to about $10^{-6}$ torr. Stencils for electrode deposition may be prepared by chemical milling. Initially, an optical transparency may be prepared using linographic methods, photographic methods, photolaser plotter methods, or the like. The optical transparency has a black outline of the electrode array. The transparency may be placed over sheet metal which has been previously coated with a positive photoresist emulsion. The transparency-emulsion-metal sandwich is then exposed to light and etched in an acid bath. Alternative methods for preparing electrodes on insulating substrates include painting with silver paint, resilvering processes, and silk screening methods.

Preparation of electrodes by silver painting involves directly painting pairs of electrodes over a polymer coated insulating substrate. Prior to painting, the quality of the film is inspected by fluorescence microscopy. Intact polymer films appear brightly orange using a rhodamine filter. For example, one may lightly paint 10–15 mm of the middle portion of a wooden applicator with silver paint. One secures the ends of the applicator with the finger and thumb and gently rolls the paint portion over the film to create an electrode about 2 mm in width. The applicator is used again to generate a parallel electrode approximately 3 mm away. Copper adhesive strip pieces may then be employed for attaching to the silver electrodes to an electrical circuit for electrical measurements. Silver paint may then be coated over the top of the copper strip in contact with the silver electrode.

Another method for preparing electrodes involves coating a glass substrate with a metal to create a front surface coat. Typical metals include chrome, silver, gold, platinum, nickel, alloys, oxides such as indium tin oxide, conducting polymers and inorganic substances. A photoresist film, negative or positive is deposited over the coat by spraying, laminating, dipping or the like onto the metal surface. A master mask is created by computer-aided design using high resolution techniques. Illumination or photoactivation with UV or white light, depending on the film composition, may be employed. The photoresist is then developed, using developing reagents such as caustic soda to remove the unexposed areas of a negative photoresist. Chemical etching will subsequently remove the unprotected metal. Cleaning off residual photoresist material may be accomplished using 10% NaOH for 3–5 minutes. The rinse steps include 10% detergent, rinsing 2–3 times in 10–20 megaOhms water, and then rinsing in high purity water and organic solvents. The electrode may be heated to remove any surface water. Heating is accomplished using a dust-free oven at temperatures ranging from 30–150° C. from between 30 seconds to 1 hour. The polymeric film prepared as described above is then transferred to the substrate-electrode so as to overlap the electrodes. Transfer is achieved by methods described above.

The metal electrodes may be sealed against contact with water. Various materials may be used to provide for insulation from water, such as parafilm, hemeseal, rubber silicone, rubber cement, UV curable materials including acrylates, cyanoacrylates, waxes, fluorinated aliphatic compounds, glues, teflons, or other commercially available sealants. For parafilm, the film is placed over the electrode, the film is compressed to remove any air bubbles and the wafer warmed to allow the parafilm to soften and coat the electrodes. The other sealants may be coated onto the electrodes and, when appropriate, the chip warmed to allow for reduction in viscosity. High resolution sealing electrodes can be accomplished by vapor deposition processes, sputtering, or the like. For vapor deposition, a stencil with openings symmetric to the metal electrode traces on the substrate, but slightly broader than the metal traces, is placed above the polymer coated electrode surface. The substrate and mask are placed in a vapor deposition apparatus and then an insulating material, such as silicon oxide is vapor deposited in such a way that the electrode is completely coated with the insulating material. The insulating material should extend slightly past the electrode edge so that it completely isolates the electrode from the environment and leaves the polymer film between electrodes uncoated.

After completion of the insulation, the lipid film may then be activated. Activation will depend upon the nature of the molecule coupled to the lipid and the molecule to be bound. At this point, the dry biosensor wafer comprises the insulating substrate, polymer film with attached molecule for binding, e.g., ligand, parallel metal electrodes which are sealed for moisture and metal electrically conductive leads.

The sensor is activated by specifically coupling, either directly or indirectly, the specific binding pair member to the lipids of the polymer on the electrode substrate surface. When the complementary member is an antibody, coupling of the antibody to the sensor is accomplished so that the binding sites of the antibody remain free to associate with specific antigens.

A large number of coupling pairs may be employed, where the binding may be covalent or noncovalent. Various proteins which bind specifically to a complementary ligand may be employed, such as enzymes, lectins, toxins, soluble receptors, and the like. Illustrative proteins include DHFR, streptavidin, avidin, cholera toxin, lectins, the c-H-ras oncogene product, and nucleases. For linkages with oligosaccharides, hydrazine may used, by itself or bound to a polymer, e.g., poly(acrylhydrazide). Alternatively, biotin, nucleotides, or other molecular recognition analogs, or the like may be used. Nucleic acids, such as ssDNA or RNA may be employed. Maleimide linkages may be employed for linking to a thiol containing molecule, which may be biotin, avidin, any ligand or binding protein, sulfhydryl containing polymer, a nucleic acid, or molecular recognition analogs. For example, an intact antibody, with a functional oligosaccharide moiety, may be cleaved with periodic acid, and the resulting aldehyde reacted with the hydrazine under reductive conditions to form a stable carbon-nitrogen bond. For providing sulfhydryl groups to react with a maleimide, the antibody may be reduced at the hinge region, partially cleaved at the hinge region, or proteolytically cleaved near the hinge region for forming a thio ether with the activated olefin. In each case, care will be taken in selecting the method of linkage to ensure that the desired sites for binding to the complementary member of the specific binding pair are available for binding. Alternatively, sulfhydryl surfactants may be attached to sulfhydryl groups on the antibody molecules.

When the binding molecule should be maintained in an aqueous environment, the following procedure is found to be useful and may be treated as exemplary. An aqueous medium is formed, which is normally buffered at a pH in the range of about 4 to 9, preferably from about 5 to 9. The salt concentration will generally be in the range of about 10 mM to 1 molar. Illustrative buffers include phosphate, borate, barbitron, carbonate, Tris, MOPS, MES, etc. Illustrative buffer compositions include phosphate buffered saline; 138 mM NaCl, 50 mM potassium phosphate, pH 7.2; 200 mM sodium borate, pH 8.2. It is found that PBS favors monolayers and cadmium stabilizes the layer. The concentration of the multivalent cations will depend to some degree upon the nature of the cation, generally ranging from about 0.1 to 200 mM, more usually from about 10 to 100 mM and will be included in the determination of total salt concentration. After submersing the polymer surface in an aqueous buffer containing from about 10–140 mM NaCl, 4–40 mM tris pH 6.5-7.5 as well as any additional appropriate coupling reagents and receptors, the reaction mixture is allowed to stand for sufficient time for completion of reaction, followed by washing. After activation with the complementary pair member, the biosensor will normally be covered for storage. The cover will be removable and will be removed prior to use. Various films may be used to seal the biosensor in a protective environment.

For carrying out an assay, the sample may be introduced onto the biosensor surface by direct injection into a reservoir buffer covering the sensor surface, by capillary action through a shallow flow cell covering the sensor, by fluid pumping through a flow cell, by gas phase adsorption and diffusion onto a wetted surface covering the sensor surface, or the like. For detecting extremely low concentrations of analyte, for example, less than about $10^{-12}$ M, the flow cell method is preferred, since it allows a large volume of sample to pass over the sensor surface so as to concentrate the specific binding member on the surface. At higher concentrations, the reservoir sensor configuration is useful, because the diffusion rate becomes less of a factor.

On line monitoring of various biological processes, in vitro events and commercial processes is accomplished by placing a flow cell apparatus over the sensor surface. As the fluid is passed over the sensor surface, the analyte from solution binds to specific receptors on the sensor.

Methods for signal generation will include direct and competitive antibody/antigen binding. Signals will be generated, for example, from antigen binding to biosensors, where the antibodies have been immobilized on the biosensor surface such that their antigen-binding sites are free for binding. Competition binding assays are used for small, usually monovalent analytes including proteins, peptides, oligosaccharides, oligonucleotides, drugs, and other small ligands. Competition assays involve the use of mono- or multivalent ligands for signal amplification.

The cellular expression systems can be utilized to form naturally occurring surfactant linked proteins which can be directly incorporated into the surfactant film. Bacteria or mammalian cells can be fed non-natural polymerizable surfactants, such as diacetylenic myristic acid, in place of natural surfactants. One such example of a cellular expression system is the myrstioylation pathway in which single acyl chains are biochemically coupled to polypeptides. Another example is the use of the phosphatidylinositol expression pathway. This pathway can be used to express soluble forms of protein receptors attached to phosphatidylinositol through an oligosaccharide moiety. If cells are fed with non-natural polymerizable phosphatidylinositols or polymerizable fatty acids, then the isolated protein/-receptor-oligosaccharide-linker-phosphatidylinositol can be used directly in the polymerizable surfactant film.

Depending upon the particular combination which is bound to the surface, a wide variety of different physical events may result, which allow for detection of a signal. The signal will result from perturbation of the polymerized surfactant layer resulting in a change in electrical, optical or structural properties of the polymerized surfactant layer. Where the analyte is small and its binding to an analyte binding molecule may have a small effect on the polymer layer, with little or no perturbation so as to prevent accurate detection, various methods may be used for signal enhancement. For example, signal amplification may be obtained through the optimization of the electrode configuration or by increasing the number of sensors in an array for increased statistical accuracy. Sensor arrays may be condensed with up to a thousand per square inch. Alternatively, the distance between the two electrodes may be decreased. An increase in the ratio of the length of the area between two electrodes to the width between the electrodes corresponds to a linear increase in the conductivity of the film.

Different types of assays can be designed. In the case of DNA assays, single-stranded DNA is immobilized in the film using one or two points of attachment. The attachment may be covalent or noncovalent, e.g., biotin, avidin, hybridization, etc. When the sample containing a complementary strand of DNA is added, DNA duplexing leads to signal generation. In the case of viral assay, virus capsid or envelope may bind directly to immobilized antibody. Macromolecules will be assayed in a similar fashion to the viral assay. For serology, the same principle applies, but antigen is immobilized, and antibody is measured. Alpha-galactose-1,4-betagalactose, immobilized in the polymer film, can bind to receptors of P. Fimbriea bacteria. Competition assays may be used for small molecules, in a displacement mode, where the competition occurs directly on the surface of the film, or in a more direct fashion, where a polyvalent cross-reacting moriety and the competitor analyte are added simultaneously to the biosensor.

Various systems may be employed for detecting a variety of analytes. For example, with an antigen attached to the polymer, one may provide for a competition assay between the antigen on the polymer and the analyte antigen for a receptor, e.g., an antibody. Alternatively, polyethylene glycol packing around the analyte molecule bound to the film may be employed, where analyte binding will displace the glycol to cause perturbation of the film. This assay avoids the need for competition. By having polyethylens glycol chains as a polar terminus of the surfactant, these molecules may align to form an ordered assay. Binding of the analyte may perturb the orderly packing leading to a structural change in the polymer layer. With polyvalent antigens, cocking may be achieved, where cocking intends that the binding of the polyvalent antigen results in bending of the film with a change in conformation of the polymer. The multivalent antigens may be prepared by chemically cross-linked antigens to beads, polymerized liposomes, macromolecular assemblies, chemically cross-linked molecules, chemically synthesized polyvalent molecules, or the like. Alternatively, drag/flow particles may be involved, where the particles compete with the analyte for binding to the surface. By having a flow of liquid past the particles, the polymer organization may be modified, with a change in signal. Another technique may involve dopant releasing complexes, such as micron sponges, polymerized liposomes, macromolecular complexes, or self-doping polymers. The presence of the dopant interacting with the surfactant polymer will provide for a change in the signal. Various tension devices may be employed, based on the use of actin and myosin. Thus, tension filaments or traversing actin filaments may be employed, with a resulting change in the conformation of the surfactant polymer.

The piezoelectric properties of protein/ surfactant films may be exploited for the purpose of analyte detection. Macromolecular crystalline assemblies have specific resonance frequencies which depend on the mass of the assembly, crystalline space group symmetry, and electrical fields in which the assemblies are placed. Vibrational frequency monitoring can be employed for the purpose of determining frequency shifts before and after analyte molecules bind to the macromolecular assembly.

Antiidotypes may be employed as divalent and cocking probes, where antibodies may be bound to the surfactant polymer and binding of the ligand to the antibody would inhibit the binding of the antiidotype. The polyvalence of the antiidotype would result in crosslinking of the antibody bound to the surfactant and modification of the conformation of the polymer.

Divalent linker molecules with natural ligands attached at the end of a linker moiety can be used to prestrain the receptor/organic conducting layer. Divalent binding results in a sterically strained surface if the linker between the ligands is somewhat inflexible, e.g., cyclic molecules, particularly aromatic linkers. Strain on the polymerized surfactant layer increases as the rigidity of the linker and the affinity between the ligand and receptor are increased. Divalent molecules may be used in competitive analyte assays where the monovalent analyte of interest is eluted onto a prestrained surface. As the divalent moiety is displaced by the monovalent analyte, strain is released and the electrical and optical properties of the film change measurably.

Conduction particles may be employed, where an antigen may be attached to the conduction particle, or antibodies may be bound to caged gold compounds, or metal particles, such as metal complexes, e.g., gold or tungsten.

Tethered antibodies may be employed, where the antibody binds to an antigen linked film through its binding site and is chemically coupled through a functional group on the antibody. The binding of the antibody to the antigen results in a change in the conformation of the polymer. Where the film bound antigen competes with antigen in the sample, there will be a different degree of binding of the surfactant-film-linked antigen to the antibody, depending upon the amount of antigen in the sample.

A strain on the polymer may be created by providing for antigen attached to polymer, particularly where a molecular cantilever may be created by microfabrication techniques. Miniature cantilevers can be micromachined such that the tip of the cantilever is placed in close proximity of the protein/polymer surface. If one of the binding members is attached to the cantilever tip and the second member is attached to the protein/polymer film, then direct binding occurs between the tip and the surface. The cantilever acts as a tension spring which when bound to the protein/ polymer film creates an intense strain on the film. Tension is released when the analyte is eluted onto the film surface and competes for binding with one of the binding pair members. Alternatively, a drum membrane may be created by a similar method. Light pulse systems may be employed to increase the film conductivity, to check the quality of the polymer film during manufacturing procedures, to stabilize signal or to drown out transient noise.

Perturbations, e.g., change in conformation of the polymerized layer, may be detected by changes in the electrical properties of the film. Thus, by providing for a voltage drop across the surfactant layer, changes in the voltage may be detected with a galvanometer, high impedence ohm-meter, amp-meter or voltmeter. Other electrical characteristics which may be detected include time domain reflectometry which involves the use of high speed, high frequency radar type pulses and frequency domain responses where spectral frequency patterning can be monitored as a function of analyte binding to the film surface. Electrical alternating current measurements are convenient for filtering out background noise due to nonspecific matrix effects. A useful circuit is comprised of a port to insert the biosensor chip, a power supply, an electrical amplifier, an analog/digital converter, a channel multiplex system, computer interface components including software and circuit boards, a computer, display terminal, and a printer. Designs for instrumentation include hand held devices which have all of the signal processing capabilities necessary for accurate data analysis.

A number of both linear and non-linear optically based techniques may be incorporated into the measurement format. The techniques rely on an ordered polymer layer in conjunction with a bound layer, which may be crystalline or non-crystalline, particularly a protein layer, as a means of signal amplification. Thus, either ordered or non-ordered protein layers may be employed.

Linear optical devices may be based upon changes in the fluorescence absorption and reflectivity properties of the thin film upon analyte binding, photoinjection of charge carriers, or the like. In addition, changes in the optical birefringence and circular dichroic properties may be monitored. For shifts in fluorescence absorption or reflectivity, it is noted that the highly conjugated polydiacteylene polymer backbone has unique spectral properties which are dictated by the local electronic environment. By monitoring the fluorescence absorption shift induced by the binding of an analyte to ligands specifically attached to the polymer, a quantitative correlation to the analyte concentration may be made. For photoinjection of charged carriers, application of a prepulse of light to a conducting polymer film produces a transient electrical decay which is characteristic of the mean free path of the charged carriers prior to recombination. The binding of an analyte and subsequent kinking of the film reduces the mean free path of the carriers. This change may be sensitively monitored using a standard transient photoconductivity measurements or performing the Fourier transform of the transient electrical decay.

For birefringence, a system of aligned molecules is optically birefringent and will rotate the polarization of incident radiation in a defined amount. The binding of analyte molecules to the polymer/protein film alters the molecular alignment of analyte binding molecules within the film. The molecular re-orientation results in a change in birefringence which is in turn manifested as a unique rotation of the linearly polarized light.

Circular dichrosim (CD) may be employed for analyte detection. Whereas optical birefringence monitors the change in the "real" part of the index of refaction, CD can be used to measure the "imaginary" part of the index of refraction. CD may be used by determining the degree of ellipticity of light after it is passed through the protein/polymer film. The CD spectrum of the film can be measured before, during, and after analyte binding occurs. Analyte binding modulates the optical anisotropic properties of the film which in turn leads to observable shifts in the CD spectrum.

For non-linear optical devices, laser-induced phonon spectroscopy (LIPS), surface harmonic generation or optical Kerr effect may be employed. The LIPS technique involves a transient holographic grating technique, which is a form of four-wave mixing providing ultrasensitive information about the bulk mechanical and vibrational structure of liquids and solids. Binding of the analyte of interest to either the protein/polymer film or macromolecular complexes in solution will significantly alter the phonon structure of the material and therefore manifest itself directly into the transient grating observable. Surface harmonic generation is as a result of a fundamental non-linear light-matter interaction in non-centrosymmetric crystals resulting in the conversion of the incident radiation into radiation at twice the frequency. This technique is inherently surface sensitive, since the surface region must be non-centrosymmetric. Binding of an analyte to the surface of a film changes the non-linear optical properties to significantly alter the intensity of the second harmonic signal, which may be observed with a photodector.

Finally, the optical Kerr effect may be used to monitor the optical Kerr effect with nanosecond time resolution. The dynamics of the reorientation of molecules (in the liquid phase) upon analyte binding, manifest themselves directly into the transient grating observable.

Analyte detection measurements may also be accomplished with the use of new microscopic techniques such as atomic force microscopy [O. Marti, H. O. Ribi, B. Drake, T. R. Albrecht, C. F. Quate, and P. K. Hansma, Science (1988) 239:50–52], and scanning tunneling microscopy [C. F. Quate, Phys. Today (1986) 39:26]. These methods may be used to probe surface and electronic structures of the protein/polymer films. Analyte detection is accomplished by visually observing the film structure before, during, and after the analyte binds to the surface. Optical filtering methods can be employed to enhance the apparent structural changes in the film.

For further understanding of the invention, the drawings will now be considered.

In FIGS. 1A–1E depict schematic views of the process of preparation of a biosensor in accordance with the subject invention. The first step involves vapor deposition of metal electrodes on an insulating surface, where onto a wafer 10 is vapor deposited metal electrodes 12, where the site of deposition is controlled by screen 14. The ultrathin conducting polymer 16 is then coated over the electrodes 12 and the space 18 on the wafer 10. Insulation is then achieved by coating the region around the electrodes 12 with insulating material 20, where screen 22 directs the regions which are coated with the sealant 20. The surfactant polymer film 16 is then activated with receptors 24 followed by protective sealing with film 26.

In FIG. 2 is depicted a diagrammatic design of the circuit and biosensor. The insulating support 30 supports electrodes 32 and electrode seal and water barrier 34. To the surfactant polymer layer 36 is bound protein receptors 38. Electrodes 32 are connected through wires 40 and 42 to a source of power 44 and a meter 46 for measuring changes in electrical signal. Buffer 48 is placed in the area defined by the water barrier 34 and the protein 38 for receipt of the analyte.

The following examples are offered by way of illustration and not by way of limitation.

EXAMPLES

The biosensor device was prepared as follows.

For various experiments, surfactant-linked ligands were prepared using condensation reactions involving an activated carboxylic acid group and a nucleophilic amine or hydroxyl. 10,12-pentacosadiynoic acid was activated with trimethylacetylchloride under anhydrous conditions to form the active asymmetric anhydride. The anhydride was treated with excess ethylene diamine or ethanolamine (in situ) to form ethylenediamino-10,12-pentacosadiynamide    EDA- PDA or ethanolamine-10,12-pentacosadiynamide EA-PDA, respectively. 1.5 mole equivalents of riethylamine were added as a catalytic base. Reactions were allowed to proceed for 3 hours at room temperature. EDA-PDA or EA-PDA were chromatographically purified using a silica gel column and a chloroform/methanol gradient. EDA-PDA or EA-PDA were condensed with free carboxylic acid containing ligands (chemically activated as above) to form the ligand-linked polymerizable surfactants. Representative examples of ligand linked surfactants which were prepared by this method for the purpose of fabricating biosensors include: 2,4-dinitrophenyl-aminocaproyl-EDA-PDA; theophylline-8-butyroyl-EDA-PDA; a-galactose-1,4-b-galactose-diethyleneoxide-aminosuccinyl-EDA-PDA; biotin-aminocaproyl-EDA-PDA; N-demethylrifampicin-succinyl-EDA-PDA; and dATP-EDA-PDA.

2,4-dinitrophenyl-aminocaproyl-EDA-PDA was prepared for fabricating a biosensor specific for antidinitrophenyl antibodies. Theophylline-8-butyroyl-EDA-PDA was prepared for fabricating a biosensor specific for anti-theophylline antibodies and theophylline assays. Biotin-aminocaproyl-EDA-PDA was prepared for the purpose of fabricating biosensors which utilize streptavidine as a binding member for various assays. N-demethylrifampicin-succinyl-EDA-PDA was prepared for the purpose of fabricating biosensor to detect RNA polymerase. dATP-EDA-PDA was prepared for the purpose of fabricating biosensors to detect enzymes and other proteins which bind to dATP. a-galactose-1,4,-b-galactose-diethyleneoxideaminosuccinyl-EDA-PDA was prepared for the purpose of fabricating biosensors to detect P. Fimbrial strains of *E. coli*.

Ethanolamino-10,12-pentacosadiynamide (EA-PDA) was also prepared for the purpose of forming mixed polymerized films. Films were usually prepared with 1-10% EA-PDA and 90-99% of any ligand-linked surfactant.

One assay involved dinitrophenyl bound to the surfactant for detection of antibody to dinitrophenyl. The biosensor was prepared in the following manner. A glass microscope cover slip (22 mm × 22 mm) was alkylated by dipping it into a solution of 5% dimethylchlorosilane and 95% hexane for 5 minutes at room temperature. The cover slip was washed two times with clean chloroform and then rinsed three times with double glass distilled water. The cover slip was air dried and then dusted with a stream of clean dry nitrogen gas.

A polymerized monolayer, containing 2,4-dinitrophenyl (DNP) as the antigen, was prepared and transferred to the alkylated cover slip as follows. A glass microscope slide (precleaned and then dusted with a stream of nitrogen) was placed on a copper plate (10 cm × 10 cm square and 0.4 cm thick). 2.0 ml double glass distilled water was applied to one end of the glass slide. 2.0 microliters of a solution containing 1.0 milligram/milliliter of monomers (2.5 mole% 2,4-dinitrophenylaminocaproyl-ethylenediamine-10,12-pentacosadiynamide and 97.5 mole% ethanolamino-10,12-pentacosadiynamide) were applied to the aqueous surface from a 5 microliter micropipet at room temperature in two equal aliquots. Upon evaporation of the solvent, the monomer dried into small visible islands at the water surface. The copper plate was transferred to a preheated hot plate (approximately 200° C. on the hot plate surface). The copper plate, microscope slide, and water were heated until the islands of monomer melted and dissolved at the water surface. The copper plate was transferred after 3-5 minutes heating to prechilled aluminum block embedded in ice. The copper plate, slide and water were allowed to cool to 4° C.

The monolayer was polymerized with a UV 254 nm short wave lamp (4 watts, 200 microwatts power output at 8 inches) at a distance of 2 inches for 4 minutes. The monolayer appeared pink by eye. Transfer of the polymerized film to the alkylated glass cover slip was accomplished by holding the cover slip horizontal with a pair of fine forceps and slowly lowering the cover slip so that the hydrophobic portion of the film (the side facing air) was directly contacted. Seconds after contact was made between the cover slip and the aqueous surface, the cover slip was pulled away and allowed to air dry. The alkylated glass cover slip appeared homogenously pink after the transfer.

Silver electrodes were applied directly to the monolayer coated cover slip by direct application of silver paint to the pink polymer surface. The silver paint (electronic grade) was applied with the aid of a thin glass micropipet to create two parallel electrodes (each 8 mm in length and 2 mm wide) with a 2 mm gap between the electrodes. The final surface area between the electrodes was 16 mm squared. Adhesive copper strips were contacted to the electrodes. Electrical contact between the electrodes and the copper strips was ensured by applying small coverage of silver paint. The silver paint was allowed to air dry at room temperature for 30 minutes.

The electrodes were electrically insulated from water using a thin parafin coating (Parafilm). A strip of Parafilm (1.4 cm × 2.0 mm) was placed over each electrode to create a channel between the electrodes and so that there were no visible signs of silver paint exposed to air within the channel. The Parafilm strips were carefully pressed on the electrodes using a thin cylindrical glass rod (4.0 mm in dia.). The Parafilm was melted onto the surface of the electrodes and polymer by placing the device into an oven (125° C.) for 2 minutes. After cooling the device to room temperature, the solidified Parafilm formed a water tight barrier over the electrodes.

The biosensor device was tested by attaching one copper test lead to the positive terminal of a 10 volt DC power supply and the other to one of three input leads on an electrometer (Kelthly 640). The circuit was completed by connecting other electrometer input leads to power supply ground and negative voltage terminals. The electrometer output (negative 1.0 volts to positive 1.0 volts) was connected to an A/D converter board which was interfaced with a desk top computer. Electrometer outputs were digitized, converted to actual units of amperes, as measured by the electrometer, and displayed on a color graphics display screen.

Prior to performing a biosensor assay, the electrometer settings were adjusted to a range setting of $1.0 \times 10^{-8}$ amphere. The electrometer was calibrated with the zero check switch. The sensitivity was placed to setting 2. The base line current of the biosensor device was 4.0 pico amps. The electrical conductivity of the device was inspected by flashing pulses of intense visible light on the polymer surface at a distance of 3 inches.

Buffer was placed on the biosensor (tris pH 7.0 with 140 mM NaCl). The assay procedure involved placing 100 microliters of buffer on the biosensor between the electrodes and within the channel. The reliability of the sensor was tested by flashing pulses of intense visible light at 1 inch distance from the sensor surface. Each light pulse gave a 100-fold increase in current above background. Once the integrity of the film was established, antitdinitrophenyl antibodies (one microliter of a one milligram/milliliter solution of antibody) were microinjected into the buffered solution. Initially a flat base line of 4.0 picoamps was observed. The base line remained stable for several seconds and then a distinct immediate rise in the current to 9.0 picoamps was recorded.

A second assay involved theophylline bound to the surfactant for the detection of an antibody to theophylline. 100 microliters of buffer (10 mM tris pH 7.0, 120 mM NaCl) were placed over the sensor. Photoresponses were monitored as above. Current increases of 100-fold above background were recorded. Once the integrity of the film was established, antitheopylline antibodies (one microliter of one milligram protein/milliliter solution) were microinjected into the buffered solution. Initially a flat base line of 3.0 picoamps was observed. The base line remained stable for several seconds and then a distinct immediate rise in the current to 8.0 picoamps was recorded within 2 min. The new base line remained stable for 30 more min. at which time the assay was terminated.

A third assay involved biotin bound to the surfactant for the detection of avidin. 100 microliters of buffer (same as above) were placed over the sensor. Photoresponses were monitored as before. Current increases from picoamps to nanoamps were recorded. Once the integrity of the film was established, avidin (one microliter of one milligram protein/milliliter solution) was microinjected into the buffered solution. Initially a flat base line of picoamps was observed. The base line remained stable for several seconds and then a distinct immediate 3-fold rise in the current above background was recorded within one minute. The new base line remained stable for 30 more min. at which time the assay was terminated.

A fourth assay involved the use of fluoresence measurements for the detection of antitheophylline antibodies on a sensor with theophylline bound to the polymer film. The sensor was placed under a fluorescence microsope objective such that the polymer film could be viewed at 75 times magnification using a rhodamine filter. 500 microliters of a buffer solution was placed on the film so that the microscope objective was immersed in the buffer. The film appeared dull orange in color and intensity. 3 microliters of a 1.0 milligram/milliliter solution of antitheophylline antibodies were microinjected into the buffer. Immediately upon injection, the intensity of fluoresence increased by 75%, and the dull orange film became brighter in appearance. A control film which contained no theophylline was unaffected by the antitheophylline antibody.

It is evident from the above results, that a sensitive technique is provided for the detection of a wide range of analytes. Numerous different techniques may be employed for detecting an electrical or light signal associated with a change in the properties of a surfactant polyunsaturated polymer. By employing different protocols, the analytes of interest may range from haptens and antigens, to aggregations, such as viruses, cells, or the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A biosensor comprising a plurality of layers:
   a first electrically non-conductive support providing mechanical rigidity to said biosensor comprising at least two spaced apart electrical leads coated on a first surface of said support;
   an electrically conducting organic polymerized crystalline surfactant layer coating said first surface between said electrical leads and comprising electrical contact portions in electrical contact with said electrical leads, said organic polymerized crystalline surfactant layer prepared from addition polymerizable conjugated diyne surfactant monomers of at least 12 carbon atoms and produced by the crystallization of said surfactant monomers and the polymerization of surfactant diynes to produce a conjugated polymer with each monomer having a hydrophilic terminum distal to said support;
   a sealing coating over said electrical contact portions to protect said electrical contact portions from contact with water; and
   an organic molecule layer bound to said organic polymerized crystalline surfactant layer at said hydrophilic termini, said organic molecule layer comprising a member of a specific binding pair for binding to a complementary member in an aqueous medium.

2. A biosensor according to claim 1, wherein said bound organic molecule layer is a layer of receptors.

3. A biosensor according to claim 1, wherein said surfactant diyne monomers have an aliphatic chain of from 6 to 100 carbon atoms.

4. A biosensor according to claim 1, wherein said organic molecule layer is bound to said surfactant layer through a complex of complementary binding members.

5. A biosensor according to claim 1, wherein said organic molecule layer is directly bound to said surfactant layer by covalent bonds.

6. A biosensor according to claim 1, wherein said support is transparent and further comprises a reflective layer on a second surface opposite said first surface.

7. A biosensor according to claim 1, wherein said organic molecule layer is a substantially oriented layer of proteins.

8. A biosensor according to claim 1, wherein said organic molecule layer is a layer of haptens.

* * * * *